United States Patent [19]

Graham et al.

[11] 4,005,192
[45] Jan. 25, 1977

[54] COMPOSITION IN SUBSTANTIALLY RIGID BLOCK FORM FOR CONTROLLING OR PREVENTING BLOAT IN ANIMALS

[75] Inventors: Clifford Arthur Andrew Graham, Nunawading; Kevin Lawrence Linehan, Burwood East, both of Australia

[73] Assignee: ICI Australia Limited, Melbourne, Australia

[22] Filed: July 17, 1974

[21] Appl. No.: 489,437

[30] Foreign Application Priority Data

July 27, 1973  Australia .......................... 4265/73

[52] U.S. Cl. .................. 424/157; 424/14; 424/180; 424/342
[51] Int. Cl.² ................ A61K 33/08; A61K 31/70; A61K 31/08
[58] Field of Search ............ 424/342, 157, 14, 180

[56] References Cited

UNITED STATES PATENTS

| | | | |
|---|---|---|---|
| 3,000,784 | 9/1961 | Todd | 424/247 |
| 3,248,289 | 4/1966 | Shinozaki et al. | 424/342 |
| 3,288,676 | 11/1966 | Kauzal | 424/247 |
| 3,465,083 | 9/1969 | Bartley et al. | 424/342 |

OTHER PUBLICATIONS

Winslow–Veterinary Materia Medical & Therapeutics, eighth edit. (1919), p. 133.

*Primary Examiner*—Sam Rosen
*Attorney, Agent, or Firm*—Cushman, Darby & Cushman

[57] ABSTRACT

A new therapeutic composition of matter effective in controlling or preventing bloat in ruminant animals, which new therapeutic composition of matter is in the form of a substantially rigid block and comprises a reaction product of molasses, magnesium oxide, and a nonionic polyoxyalkylene surface active compound.

5 Claims, No Drawings

COMPOSITION IN SUBSTANTIALLY RIGID BLOCK FORM FOR CONTROLLING OR PREVENTING BLOAT IN ANIMALS

This invention relates to a therapeutic supplementary feed composition for animals, especially ruminant animals such as sheep and cattle. In particular our invention relates to a novel therapeutic feed supplement composition in the form of a substantially rigid block which is valuable for the control or prevention of bloat in animals, especially ruminants. In addition our invention relates to a process for the preparation of the said rigid therapeutic feed supplement blocks.

By the term "substantially rigid block" we mean a block which does not undergo any appreciable plastic flow under its own weight, and which retains its shape over long periods of time in the field under rural conditions.

Bloat is a condition occurring in adult ruminants and is thought to be caused by inability of the animals to expell, via the normal muscular contraction mechanism, the large volumes of gas generated within their rumen in the course of the anaerobic microbial fermentation processes taking place therein. In cattle typical symptoms of severe bloat are a distended abdomen, staggering gait, bellowing, and frequent urination and defaecation. Eventually the animals may have breathing difficulty and suffer heart failure. The disease has been reported in many countries, and is widespread in Australia particularly in the southern states.

It is known that bloat in animals may be controlled or prevented by the administration of a suitable effective quantity of a nonionic polyoxyalkylene surface active compound. Administration may be affected by drenching the animals with a solution or dispersion of the said polyoxyalkylene compound, by means of the addition of the said polyoxyalkylene compound to drinking water in troughs, by admixture of the said polyoxyalkylene compound with inert carriers such as vermiculite and bentonite, by admixture of the said polyoxyalkylene compound with feed stuffs, or by incorporation of the said polyoxyalkylene compound into sustained release gels formed into shapes or included in capsules which are difficult to reject from the rumen.

However these prior art methods of administering a suitable source of nonionic polyoxyalkylene surface active agents to ruminants for the prophylaxis of bloat suffer from several disadvantages. Thus liquid formulations, for example, a solution, dispersion, or suspension of a nonionic polyoxyalkylene compound in a liquid carrier such as water, are inconvenient to formulate, handle, and transport under rural conditions, and the formulations are frequently not stable in the field over long periods of time. Powdered formulations comprising, for example, a suitable mixture of a nonionic polyoxyalkylene compound and vermiculite, are found to be wasteful when used in the field, since they may be leached by rain and dispersing by winds. Furthermore, both these types of formulation are frequently found to be unpalatable to the animals, and in addition, when these methods of administration are used it is difficult to regulate the animals' intake of polyoxyalkylene compound.

Controlled administration of the source of polyoxyalkylene compound is very desirable, since for example for effective treatment or prophylaxis of bloat in cattle using feed supplement compositions comprising a nonionic polyoxyalkylene surface active compound, each beast should ingest about 10 g of the polyoxyalkylene compound per day. Amounts substantially lower than this may not reduce the incidence of bloat.

Oral administration of shaped sustained release gels or capsules comprising nonionic polyoxyalkylene surface active compounds, while sometimes being a suitable technique for control of bloat in readily accessible groups of animals, for example dairy cattle herds, becomes an impractical technique for larger groups of animals scattered over vast areas, for example beef cattle herds.

We have now found a new therapeutic composition of matter which may be shaped in the form of a substantially rigid block and comprises a reaction product of molasses, magnesium oxide, and a nonionic polyoxyalkylene surface active compound, obtained by reacting each of these ingredients in the quantities and manner described hereinbelow, which new therapeutic composition of matter is effective in reducing or preventing the occurrence of bloat in animals, especially sheep and cattle, and which substantially overcomes the difficulties hitherto associated with this prophylaxis as described above. We have found that such blocks may be prepared conveniently if a chosen quantity of molasses is heated to a temperature sufficiently high to render it in a mobile state, adding a suitable quantity of magnesium oxide and at least one nonionic surface active compound, these ingredients being added together or separately, blending the mixture thoroughly, and maintaining the resultant blend at a controlled temperature until the evolution of self-generated heat from the blended mixture has ceased substantially and the blended mixture has been converted to a substantially rigid form. Additional rigidity may also be acquired by the blocks on prolonged storage.

Accordingly we provide a new therapeutic composition of matter, effective in controlling or preventing bloat in ruminant animals, which new therapeutic composition of matter is in the form of a substantially rigid block and comprises a reaction product of molasses, magnesium oxide, and a nonionic polyoxyalkylene surface active compound.

We also provide a method of controlling or preventing bloat in ruminant animals, which method comprises supplying to said animals in a therapeutically effective quantity a feed supplement composition in the form of a rigid block and comprising a reaction product of molasses, magnesium oxide, and a nonionic polyoxyalkylene surface active compound.

The nature of the nonionic polyoxyalkylene surface active compound utilized in the preparation of the novel therapeutic compositions according to the present invention is not narrowly critical. A preferred class of such compounds are the polyoxyalkylene ethers of general formula:

R — O — Polyoxyalkylene wherein R is selected from the group consisting of linear alkyl, branched alkyl, alkyl substituted aryl, aryl substituted alkyl, linear unsaturated hydrocarbyl, and branched chain unsaturated hydrocarbyl; and the polyoxyalkylene moeity comprises a homopolymer of a compound selected from the group consisting of ethylene oxide, propylene oxide, and butylene oxide, or a block or random copolymer of at least two of these alkylene oxides.

A preferred sub-class of our preferred class of nonionic polyoxyalkylene surface active compounds is that sub-class having the generic formula:

$$R - O - (\text{alkylene} - O)_n c - H$$

wherein R represents an alkyl radical of 1 to 20 carbon atoms, and the formula $-(\text{alkylene-O})_n$ represents a random distribution of oxyethylene and oxypropylene groups in the ratio of from 95% by weight oxyethylene/5% by weight oxypropylene to 5% by weight oxyethylene/95% by weight oxypropylene and wherein said oxyethylene and oxypropylene groups comprise about 60 to 90% by weight of said polyoxyalkylene ethers.

A more preferred sub-class of our preferred class of nonionic polyoxyalkylene surface active compounds is that sub-class characterized by the general formula:

$$R^1 - O + CH_2CH_2 - O +_n H$$

wherein $R^1$ is a linear $C_{9-18}$ alkyl group and $n$ lies in the range 10 to 30 inclusive.

A particularly preferred nonionic polyoxyalkylene surface active composition for use in the preparation of therapeutic feed supplement compositions according to the present invention is obtained by condensing 'Synprol' alcohol (Registered Trade Mark of ICI Australia Ltd. for a 45% linear, 67% $C_{13}$, 33% $C_{15}$ alcohol) randomly with 11.75 moles of ethylene oxide and 2.9 moles of propylene oxide.

The nature of the magnesium oxide used to prepare the novel therapeutic feed supplement compositions of our invention is also not narrowly critical, but it is preferred that the magnesium oxide should be of a sufficiently reactive grade such that it reacts substantially completely, as described hereinbelow, within a reasonable length of time, say less than 6 hours. Whilst pure magnesium oxide may be used the cost of such a raw material is comparatively high. The presence of small amounts of impurities such as are normally found in commercially available grades of magnesium oxide can be tolerated in our compositions. Commercially available grades of reactive magnesiun oxide having the advantage of a lower cost than pure magnesium oxide are eminently suitable for use in our compositions. Typical of such commercial grades of magnesium oxide suitable for use in the preparation of the novel compositions of our invention are those known as caustic-burned magnesias, produced by calcining magnesite, dolomite, or magnesium hydroxide at temperatures less than 900° C. Particularly suitable magnesium oxide materials are "Causmag" Superfine XLF, Causmag Grade AL3, and Causmag Grade AL4 (Causmag is a trade name for a proprietary brand of magnesium oxide) available from the Causmag Ore Co Pty Ltd of Young, N.S.W., Australia.). The molasses used to prepare the compositions of our invention may be derived from any of the more common sources such as sugar cane, sugar beet, or even wood, but it is preferably that obtained from cane sugar.

We also provide a process for the preparation of the novel therapeutic feed supplement compositions of our invention as described hereinabove, which process comprises charging a selected quantity of molasses to a suitable reaction vessel fitted with a mixing device; heating said molasses to a temperature not in excess of 90° C, preferably to a temperature in the range from 65° to 75° C; adding a suitable quantity of magnesium oxide and a suitable quantity of a nonionic polyoxyalkylene surface active compound, either separately or together, to the said reaction vessel; blending said molasses, magnesium oxide, and polyoxyalkylene compound for a sufficient length of time so as to form a substantially uniform reaction mixture whilst maintaining the temperature of said mixture at a temperature not in excess of 90° C; optionally adding water during said blending step; transferring said reaction mixture to a mould; placing said mould containing said reaction mixture into a device capable of maintaining the temperature of the said reaction mixture at a desired temperature in the range of from 45° to 90° C., preferably in the range of from 55° to 70° C, such as an air-circulated oven or suitably insulated container, and allowing the mould to stand therein until the evolution of heat from the reaction mixture has substantially ceased and the said reaction mixture has become rigid. The mould is then removed and allowed to cool to the ambient temperature, whereupon the reaction mixture is released from the mould in the form of a rigid block.

The size and shape of the said moulds is not narrowly critical, and therapeutic compositions of matter according to the present invention may be in forms ranging from small cubes or pellets suitable for admixture with other animal feedstuffs to large lick blocks weighing in excess of 100 lbs. For use in the field as a lick block, a therapeutic composition according to the present invention in the shape of a rectangular parallelepiped of approximate dimensions 1 × 1 × ½ feet and weighing approximately 50 lbs is convenient.

The temperature to which the molasses is heated is not narrowly critical, but it should be sufficiently high to ensure that the molasses is sufficiently fluid to be agitated. For most types of molasses, temperatures of 40° C and above, say from 65° to 75° C, are suitable. It is desirable that the temperature of the molasses be kept below 90° C to prevent undue dehydration of the molasses prior to adding the magnesium oxide and polyoxyalkylene compound.

The time required to blend and initially react the molasses, magnesium oxide, and polyoxyalkylene compound will depend to some extent on the temperature employed during the blending and reacting period and may be as little as 5 minutes and as prolonged as 6 hours. For most formulations and temperatures of reaction a period from 15 minutes to 2 hours is satisfactory. The temperature used during the blending and reacting step is conveniently between 40° and 90° C, usually from 60° to 70° C. Care should be taken in choosing the temperature used in the blending and reacting step to ensure that the reaction does not proceed at such a rate that the reaction mixture becomes too viscous to be adequately mixed. The addition of water to the reaction mixture is often beneficial in controlling viscosity. Should the chosen temperature be too high for use with a desired set of reactants the reaction mixture may even become solid in the reaction vessel. Temperatures suitable for particular mixtures may be determined by simple experiments and we have found that for most mixtures temperatures not in excess of 90° C are satisfactory.

The amount of nonionic polyoxyalkylene surface active compound used in the preparation of the novel therapeutic feed supplement compositions according to the process of our invention as described hereinabove will vary according to the particular polyoxyalkylene compound chosen, the species of animal to be treated, their state of health, the conditions under which they are kept, and the feed available to them. We have found that an amount of polyoxyalkylene compound in the range of from 5% by weight to 25% by weight based on the total weight of starting materials, when utilized to prepare our novel therapeutic feed supplement compositions according to the process described hereinabove, are very effective in controlling and preventing bloat in animals.

Our preferred novel therapeutic feed supplement compositions are prepared from 10% weight to 20% by weight of polyoxyalkylene compound based on the total weight of starting materials.

When the amount of polyoxyalkylene compound used in the process described hereinabove is below 5% by weight based on the total weight of starting materials, the efficacy against bloat of the feed supplement compositions thus produced is markedly reduced and such feed supplement compositions are generally not of practical interest.

When the amount of polyoxyalkylene compound used in the process described hereinabove exceeds 25% by weight based on the combined weight of starting materials, difficulty is experienced in obtaining a homogenous feed supplement composition and again these compositions are generally not of practical interest.

The amount of magnesium oxide used in the preparation of the novel therapeutic feed supplement compositions according to the process of our invention as described hereinabove also depends on the factors described hereinabove and in addition depends on the amount of water present in the molasses. Molasses is a product of a variable composition and its water content will vary according to its source and method of manufacture. Hence the proportion of magnesium oxide present in our compositions will depend to some extent on the type of molasses used.

Thus while suitable therapeutic feed supplement compositions according to the present invention may be prepared by the process described hereinabove from magnesium oxide present in an amount of from 5% w/w to 50% w/w based on the total weight of starting materials, we have found that more suitable therapeutic feed supplement compositions may be prepared by the process described hereinabove when the ratio of the magnesium oxide to molasses starting materials, expressed as a percentage, lies in the range 7% w/w to 30% w/w. When the magnesium oxide to molasses ratio expressed as a percentage, lies below 7% w/w it is found that the feed supplement compositions thus produced are not sufficiently rigid for practical use in the field, whilst when the magnesium oxide to molasses ratio, expressed as a percentage, is greater than 25% w/w the therapeutic feed supplement compositions thus produced are sometimes less readily accepted by certain animals.

Our preferred novel therapeutic feed supplement compositions are prepared from starting material comprising magnesium oxide present in an amount of from 5% w/w to 20% w/w based on the total weight of said starting material, and wherein the ratio of magnesium oxide to molasses, expressed as a percentage, lies in the range 10% w/w to 20% w/w inclusive.

Thus the amount of molasses utilized in the preparation of our novel therapeutic feed supplement compositions according to the process described hereinabove may also vary widely and lies in the range of from 25% by weight to 90% by weight based on the total weight of starting materials. Preferably the amount of molasses lies in the range of from 45% by weight to 75% by weight based on the total weight of starting materials.

In controlling or preventing bloat in sheep and cattle by supplementing their diet with the therapeutic feed compositions of our invention, the quantity of nonionic polyoxyalkylene surface active compound ingested by the animals can be regulated to a desired level by varying the proportions of the molasses, magnesium oxide, and polyoxyalkylene starting materials.

The molasses when used as starting material in the quantities described hereinabove to prepare the reaction product of our invention, renders our therapeutic supplementary feed blocks palatable to sheep and cattle. The palatability of our supplementary feed blocks may be increased by replacing a portion of the magnesium oxide starting material with alternative setting agents, for example gypsum, anhydrous sodium sulphate, anhydrous sodium carbonate, or mixtures of these, provided that the amount of magnesium oxide, expressed as a percentage of the amount of molasses starting material, does not fall below 7% w/w. Thus a therapeutic feed lick block according to the present invention and prepared according to the process described hereinabove from starting material comprising molasses 57% w/w, anhydrous sodium sulphate 10% w/w, magnesium oxide 8% w/w salt 15% w/w, and "Teric" 12A23 10% w/w (Teric is a Registered Trade Mark), all proportions being based on the total weight of starting material, is readily accepted by sheep and cattle and has high efficacy in preventing bloat in them. When desired and especially when the proportions of magnesium oxide and polyoxyalkylene compound in the initial reaction mixture are high, materials such as sodium chloride, or acids such as acetic acid or sulphuric acid may be incorporated in the said initial reaction mixture to further increase the palatibility of the resultant therapeutic feed block composition. Thus a supplementary feed block comprising a reaction product of molasses, magnesium oxide, and a nonionic polyoxyalkylene surface active compound, and especially when the proportion of molasses in the starting material is high, when made available to sheep and cattle is found to be consumed fairly quickly, and another therapeutic supplementary feed block can then be provided after a period of time chosen to maintain the amount of polyoxyalkylene compound in the animals' rumen at a desired level. Under rural conditions, simple field trials can determine the optimum rate of feeding of the feed blocks according to our invention which will be effective in preventing bloat under the prevailing conditions.

Where desired other ingredients may be included in the preparation of the novel therapeutic feed supplement compositions of our invention.

Thus for example additional setting or solidifying agents such as anhydrous sodium sulphate and anhydrous sodium carbonate, sources of sodium such as sodium chloride, sources of non-protein nitrogen such as urea, urea phosphate, urea sulphate, biuret, crobonylidere diurea, isobutylidere diurea or methylene diurea, or mixtures of these, sources of inorganic sulphur such as calcium sulphate, sources of calcium such as calcium carbonate, salts of trace metals such as salts or cobalt, manganese or copper, additional sources of carbohydrate such as maize germ, roughage, or crushed grain, additional sources of magnesium, such as magnesium chloride or magnesium carbonate, and additional sources of inorganic phosphate such as phosphoric acid, tricalcium phosphate, or rock phosphate, may be incorporated into the novel therapeutic feed supplement compositions of the present invention where there is a deficiency of these materials in the available feed, or where the animals' state of health requires it.

In particular, in the northern parts of Australia there are vast areas of pasture used for grazing beef cattle and which for the most part have a severe difficiency of sources of phosphate. It is thus found necessary, so as to maintain the health of the cattle and keep them in marketable condition, to make a plentiful supply of phosphate available to them. We have found that this can be conveniently done by incorporating a source of inorganic phosphate such as phosphoric acid, tricalcium phosphate, rock phosphate, or mixtures of these, into the novel therapeutic feed supplement compositions of the present invention as described hereinabove.

Preferably, as mentioned hereinabove, the source of inorganic phosphate is added simultaneously with the magnesium oxide or the nonionic polyoxyalkylene surface active compound to the molasses, in a suitable mixing device and processed in the manner described hereinabove to produce a novel therapeutic feed supplement composition in the form of a rigid block and comprising a reaction product of molasses, magnesium oxide, and a nonionic polyoxyalkylene surface active compound and comprising in addition a source of phosphate.

The quantity of the source of inorganic phosphate utililzed to produce these novel therapeutic feed supplement compositions may vary widely, and will depend on local conditions and the state of health of the cattle.

We have found for example that for use in the northern areas of Australia an amount of phosphate (as tricalcium phosphate) in the range of from 5% by weight up to 300% by weight based on the total weight of starting materials, when utilized in the preparation of our novel therapeutic feed supplement compositions, can supply the cattle feeding in these areas with sufficient phosphate to prevent them suffering the consequences of a phosphate deficiency and concurrently provide a means of combating bloat. The amount of the source of inorganic phosphate required in any particular area can be determined by simple field trials. We have also found that under these conditions the novel therapeutic feed supplement compositions of the present invention are very useful for keeping beef cattle in good health by preventing bloat, and providing an adequate amount of carbohydrate and phosphate.

Accordingly we provide as a new therapeutic composition of matter a substantially rigid block comprising a reaction product of molasses, magnesium oxide, and a nonionic polyoxyalkylene surface active compound, and which comprises in addition a source of inorganic phosphate present in an amount of from 5% by weight to 300% by weight based on the total weight of starting materials.

We also provide a process, substantially as described hereinabove, for the preparation of these novel therapeutic feed supplement compositions and wherein there is added to the molasses, prior to, simultaneously with, or after, the addition of the magnesium oxide and polyoxyalkylene compound, a quantity of a source of inorganic phosphate in the range of 5% by weight to 300% by weight based on the combined weight of starting materials.

We further provide a process of supplying animals, especially ruminants, with a source of phosphate, said process comprising supplementing the diet of the said animals with a therapeutic feed composition in the form of a rigid block comprising a reaction product of molasses, magnesium oxide, and a nonionic polyoxyalkylene surface active compound, and comprising in addition a source of inorganic phosphate as described hereinabove.

The novel therapeutic feed supplement compositions of our invention, comprising a reaction product of molasses, magnesium oxide, and a nonionic polyoxyalkylene surface active compound prepared by the process described hereinabove and in the form of a rigid block, are conveniently handled, stored, and transported, and have excellent stability and weather resistance under field conditions. In particular they resist leaching and only crumble or break up slowly under the combined effects of wind, rain, and temperature fluctuations.

The novel therapeutic feed supplement compositions of our invention are found to be effective in preventing bloat in animals, especially ruminants such as sheep and cattle, and have also been found to be useful in providing them with sustenance in those areas where natural feed is inadequate.

The compositions and processes of our invention are illustrated by, but in no way limited to, the following examples.

EXAMPLE 1

70 kg of molasses was charged into a jacketed ribbon mixer and heated to 65° C with agitation. Heating was then ceased and magnesium oxide (8.4 kg, Causmag Grade AL4) was added, followed by anhydrous sodium sulphate (12.1 kg), and then salt (18.2 kg) as slowly sprinkled onto the mixture. Then 12.1 kg of molten Teric 12A23 (Teric 12A23 is a Registered Trade Mark of ICI Australia Limited for a nonionic surface active composition obtained by condensation of one mole of a mixture of C12 – 14 linear aliphatic monohydric alcohols with approximately 23 moles of ethylene oxide.) was then poured onto the mixture, and the agitation rate was increased to ensure complete mixing. Agitation was continued for 20 minutes at 65° C, and then 20 kg of the reaction mixture was poured into each of six suitably sized polyethylene film lined cardboard boxes, and these were then immediately placed in an air circulating oven maintained at 60° C until evolution of heat from the reaction mixture had substantially ceased, and the composition in each cardboard box has become rigid.

The cardboard containers were then removed from the oven, allowed to cool to ambient temperature, and the reaction product, in the form of six rigid blocks with no tendency to plastic flow, was released from them.

EXAMPLES 2 to 6 inclusive

In each of these examples the procedure of Example 1 was substantially repeated, except that the air circulating oven was maintained at 68° C, and the quantities of molasses, magnesium oxide, and Teric 12A23, and additional ingredients used are indicated in Table 1 below.

In each case a therapeutic feed supplement composition according to the present invention and in the form of a rigid block was obtained.

These blocks showed no tendency to exhibit plastic flow, and in the field showed excellent resistance to weathering, were very effective in preventing bloat in those animals to which they were supplied, and also provided the animals with an economic means of sustenance.

TABLE I (BLOCK COMPOSITIONS (% BY WEIGHT)

| Materials | Block No. 1 | 2 | 3 | 4 |
|---|---|---|---|---|
| Molasses | 60 | 63 | 55 | 58 |
| "Teric" 12A25 | 10 | 10 | 15 | 15 |
| Salt | 15 | 15 | 15 | 15 |
| Magnesium oxide | 15 | 10 | 15 | 10 |
| Acetic Acid | — | 2 | — | 2 |

TABLE 1

| Example No. | Molasses (kg) | Magnesium oxide (kg) ("Causmag" Grade AL4) | Sodium sulphate- anhydrous (kg) | Sodium carbonate- anhydrous (kg) | "Teric" 12A23 (kg) | Salt (kg) |
|---|---|---|---|---|---|---|
| 2 | 67 | 13 | — | — | 10 | 10 |
| 3 | 60 | 15 | — | — | 10 | 15 |
| 4 | 62 | 14 | — | — | 10 | 14 |
| 5* | 63 | 10 | — | — | 10 | 15 |
| 6 | 58 | 7 | 10 | — | 10 | 15 |
| 7 | 57 | 8 | — | 10 | 10 | 15 |
| 8 | 57 | 7 | 15 | — | 10 | 15 |
| 9 | 56 | 9 | — | 10 | 10 | 15 |
| 10 | 60 | 5 | — | 10 | 10 | 15 |
| 11 | 62 | 8 | — | 10 | 10 | 10 |
| 12 | 62 | 8 | 10 | — | 10 | 10 |
| 13 | 70 | 10 | — | — | 10 | 10 |
| 14 | 65 | 15 | — | — | 10 | 10 |
| 15* | 68 | 10 | — | — | 10 | 10 |
| 16 | 68 | 12 | — | — | 10 | 10 |

*These formulations included in addition 2% w/w of acetic acid based on the total weight of starting materials.

EXAMPLE 17

TABLE 2

| | Control | | | | Blocks | | | |
|---|---|---|---|---|---|---|---|---|
| | Total 0 | Bloat 1 | Scores* 2 | No of Deaths | Total 0 | Bloat 1 | Scores 2 | No of Deaths |
| Preliminary Period 17 days | 218 | 136 | 37 | — | 225 | 132 | 34 | — |
| Treatment Period 46 days | 511 | 315 | 232 | 2** | 760 | 296 | 2 | Nil |

*The animals were observed each day and classified as follows:
0 — No bloat
1 — Mild bloat
2 — Severe bloat
The number of animals in each class each day was then summed over the period of observation.
**Two calves died - one on the 41st day and the other on the 48th day after commencement of the preliminary period.

This example describes the efficacy of solid supplementary feed lick blocks according to the present invention in preventing and controlling bloat in cattle.

Forty-six mature cows were ear tagged and scored* daily for bloat for a period of 17 days. The animals were then divided equally into 2 groups on the basis of their severity and frequency of bloating. The two groups were then placed in a paddock and separated by an electric fence. Four supplementary feed lick blocks prepared according to processes of the present invention from the starting materials listed below in Table 1, were then placed out to one group, the other group serving as controls.

The animals were then scored for a further 46 days, and the results are presented below in Table 2. It can be seen that there was an almost complete absence of severe bloat in the group of cattle treated with the supplementary feed lick blocks of the present invention.

We claim:

1. A therapeutic composition of matter in the form of a substantially rigid block for use in controlling or preventing bloat in animals, said composition comprising an effective amount of the reaction product obtained by mixing together at a temperature not in excess of 90° C molasses, magnesium oxide, and a nonionic polyoxyalkylene surface active compound and maintaining the resultant mixture at a temperature not in excess of 90° C until the evolution of self-generated heat from the mixture has ceased substantially and the mixture has been converted to a substantially rigid form, the surface active compound being one of formula

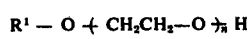

wherein $R^1$ is a linear $C_{9-18}$ alkyl group and $n$ lies in the range 10 to 30 inclusive.

2. A composition of matter according to claim 1 and comprising in addition a quantity of a source of inorganic phosphate in the range of from 5% by weight to 300% by weight based on the total weight of starting materials.

3. A method of controlling or preventing bloat in ruminant animals which method comprises supplying to said animals in a therapeutically effective quantity a feed supplement composition according to claim 1.

4. A process of supplying animals with a source of phosphate, said process comprising supplementing the diet of said animals with an effective amount of a composition according to claim 2.

5. The composition of claim 1 wherein the amount of molasses is in the range of from 45 to 75%, the amount of polyoxyalkylene compound is in the range of from 10 to 20% and the amount of magnesium oxide is in the range of 10 to 20% by weight, based on the total weight of said reactants.

* * * * *